United States Patent [19]
Zanetta et al.

[11] Patent Number: 5,225,352
[45] Date of Patent: Jul. 6, 1993

[54] AGENTS FOR THE DIAGNOSIS OF DEMYELINATING NEUROPATHIES, IN PARTICULAR MULTIPLE SCLEROSIS

[75] Inventors: Jean-Pierre Zanetta, Griesheim S/Souffel; Jean-Marie Warter, Strasbourg; Sabine Kuchler, Strasbourg; Guy Vincendon, Strasbourg, all of France

[73] Assignee: Centre National de la Recherche Scientifique, Quai Anatole, France

[21] Appl. No.: 577,884

[22] Filed: Sep. 5, 1990

[30] Foreign Application Priority Data

Sep. 6, 1989 [FR] France .................. 89 11667

[51] Int. Cl.$^5$ .......................... G01N 33/543
[52] U.S. Cl. .................. 436/518; 435/7.95; 435/975; 436/506; 436/811; 436/827; 436/828
[58] Field of Search .......... 436/518, 506, 811, 540, 436/827; 435/7.1

[56] References Cited

U.S. PATENT DOCUMENTS 4,311,686 1/1982 Angers et al. .................. 424/1

FOREIGN PATENT DOCUMENTS 0337799 4/1989 European Pat. Off. .
WO/89/005-81 1/1989 France .

OTHER PUBLICATIONS

Hukkanen et al., Medline Abs. 83193374.
Smith et al., Ann. Rev. Immunol. 1:175–210, 1983.
Kuchler, et al., Cerebellar Soluble Lectin Is Responsible for Cell Adhesion and Participates in Myelin Compaction in Cultured Rat Oligodendrocytes; Developmental Neuro Science 10: 1988; pp. 199–212.
Zanetta, et al., Isolation and Immunochemical Study of A Soluble Cerebellar Lectin Delineating Its Structure and Function; Journal of Neuro Chemistry 49: 1987; pp. 1250–1257.
Benjamin Gerson et al.; Myelin Basic Protein, Oligoclonal Bands, and IgG in Crebrospinal Fluid as Indicators of Multiple Sclerosis; Clinical Chemistry, vol. 27, No. 12, 1981; pp. 1974–1977.
The Lancet; vol. 335, Jun. 23, 1990 No. 8704; pp. 1482–1484.

Primary Examiner—Esther L. Kepplinger
Assistant Examiner—Donna C. Wortman
Attorney, Agent, or Firm—Fish & Richardson

[57] ABSTRACT

The invention relates to the use for the diagnosis of demyelinating neuropathies, in particular multiple sclerosis or MS, of endogenous lectins having an affinity for glycans rich in mannose or their protein subunits, these lectins or their subunits being immunologically related to the cerebellar soluble lectins (CSL or their protein subunits, respectively).

13 Claims, 3 Drawing Sheets

AGENTS FOR THE DIAGNOSIS OF DEMYELINATING NEUROPATHIES, IN PARTICULAR MULTIPLE SCLEROSIS

The invention relates to agents for the in vitro diagnosis of demyelinating neuropathies, in particular multiple sclerosis or MS.

Statistical studies made by the World Health Organisation show that MS is a disease which is spreading throughout the world and particularly in the regions where it is favoured which are the countries with a cold and temperate climate. 50,000 cases have been identified in France, but the actual number of cases must be higher. The same proportion of patients is found in all of the countries of Europe and North America with a cold or temperate climate, as well as in the corresponding zones of the southern hemisphere.

The study of MS has shown that various factors, genetic and/or geographic, or even infectious factors may play a role in triggering it. The nature of these agents and their mechanism of action in the triggering of MS have hitherto not been elucidated. It is accepted, however, that at a certain stage the disease develops into an autoimmune attack on the myelin in the tissues of the central nervous system with the formation of patches of degenerated myelin.

An invasion of macrophages and different types of lymphocytes and the final isolation of the patches by astrocytes are also observed.

The biochemical analyses conducted have not made it possible to identify up to now specific constituents of the myelin (whether it be lipids, nucleic acids or proteins) endowed with antigenic properties and constituting the immunological target of the antibodies produced in this disease.

After the failure of the experiments attempting to demonstrate antibodies directed against protein or major lipid antigens of the myelin in the cerebrospinal fluid of patients suffering from MS, some groups of researchers have taken an interest in the Myelin Associated Glycoprotein MAG, and then in the Myelin-Oligodendrocyte Glycoprotein MOG, without positive results being unambiguously obtained.

Another approach has consisted of investigating whether the antibodies present in the cerebrospinal fluid of patients suffering from MS are directed against viral epitopes and, in particular, retroviral epitopes of the HTLV-1 type. The results obtained have, however, shown an insufficient specificity of the reaction, since very many positive reactions have been observed in patients suffering from neurological diseases other than neuropathies.

The study made by the inventors of specific lectins binding to glycans rich in mannose has shown that they correspond to antigens specifically recognized by antibodies present in the cerebrospinal fluid and blood of patients suffering from demyelinating neuropathies and, more particularly, multiple sclerosis.

Thus, the invention relates to the use of such lectins for the in vitro diagnosis of demyelinating neuropathies.

More particularly, the aim of the invention is to provide agents for the diagnosis of these diseases, namely a method enabling them to be detected at an early stage by using the said lectins and a kit containing the material necessary to perform the diagnosis.

The invention is thus characterized by the utilization in the diagnosis of demyelinating neuropathies, in particular MS, of lectins recognizing glycans rich in mannose, or their protein subunits, these lectins or their subunits being immunologically related to the "cerebellar soluble lectin" or "CLS" or their protein subunits, respectively.

The expression "immunogically related" signifies that the endogenous lectins or their subunits are capable of forming complexes of the antigen-antibody type with the antibodies recognizing the CSL or their subunits, respectively.

The cerebellar soluble lectins or CSL are described by ZANETTA et al in the Journal of Neurochemistry, 1987, p. 1250-1257. In this article, the isolation of the CSL and its protein subunits from the cerebellum of the rat is reported. These CSL and their precursor subunits are characterized by their affinity for the glycans rich in mannose borne by glycoproteins insoluble in neutral detergents such as TRITON X-100 ®, 4-[(1,1,3,3-tetramethylbutyl)phenyl]-1-oxypolyethoxyethanol.

The subunits as obtained by extraction from the cerebellum of the rat according to this article possess molecular weights (MW) of 31.5 kDa, 33 kDa and 45 kDa.

The use as defined above has led to the development of a method for the diagnosis of multiple sclerosis and other demyelinating neuropathies characterized by the incubation of a sample taken from a patient, in particular of cerebrospinal fluid, blood or plasma fluid such as the plasma or the serum with an endogenous lectin such as that defined above under conditions permitting a reaction of the antigen-antibody type to take place, the revelation of the immunological complex formed according to the standard methods for the revelation of the immunoglobulins.

This test according to the invention offers the additional advantage of forming part of standard biomedical immunological analysis and, consequently, of entailing a moderate cost price.

As emerges from the examples given below, the results obtained by applying this test to a set of samples of cerebrospinal fluid have shown its great sensitivity as well as a remarkable specificity which make early screening of the disease possible.

Similarly, in patients presenting a clinical diagnosis of multiple sclerosis and most of whom possess anti-CSL antibodies in their cerebrospinal fluid, the presence of anti-CSL antibodies have been observed in their blood or plasma fluids such as plasma and serum.

Thus, a dilution of 1 to 1000 for example of the plasma of patients suffering from multiple sclerosis makes it possible to demonstrate the presence of anti-CSL antibodies quite unambiguously.

The significance of these results which show that the presence of these antibodies is not strictly specific for nervous tissues and that the cerebellar soluble lectins are a preferential target in MS can be appreciated.

Furthermore, it should be noted that the use of blood or plasma fluids for performing the test makes it much more practical in the sense that it entails only a blood sample which is much easier to take than a spinal puncture which requires hospitalization.

Furthermore, the test can be performed on only a few microliters of blood.

With the aid of the diagnosis performed on the basis of the method of the invention it is possible to carry out complementary examinations by having recourse, for example, to NMR (nuclear magnetic resonance) which enables disseminated lesions in the white matter to be visualized.

The endogenous lectins utilized in the diagnostic method of the invention are partially purified lectins or pure preparations.

The lectins or their subunits are widely distributed in the tissues of mammals, birds and fishes and can be isolated from these tissues according to various purification techniques but which are advantageously based on the affinity of these lectins for glycans rich in mannose.

CSL or endogenous lectins immunologically related to the CSL are used, for example CSL lectins isolated from other mammals, birds, fishes or other organisms lower down on the evolutionary scale.

As an alternative, the diagnostic method of the invention is implemented by using one or more subunits of these lectins.

Preferred subunits of CSL are those obtained by the procedure of ZANETTA et al mentioned above.

They are, in particular, subunits of 45 kDa, 33 kDa and 31.5 kDa.

The incubation of the endogenous lectins or their subunits with the sample to be tested is advantageously conducted at room temperature in a buffer.

More particularly, a buffer of pH close to neutrality and of relatively high ionic strength is used such as a buffer of the TBS type (10 mM Tris-HCl, pH 7.2 containing 0.15M of NaCl) or a buffer of the PBS type (25 mM $NaH_2PO_4$-$Na_2HPO_4$, pH 7.2 containing 0.15M of NaCl).

The revelation step of the immunoglobulins bound to the endogenous CSL lectins is advantageously carried out using either labelled anti-human-Ig immunoglobulins or labelled anti-IgG immunoglobulins or molecules of a non-immune type.

The immunoglobulins are labelled, in particular, with an enzyme or a radioactive reagent.

As enzyme, mention may be made of peroxidase, alkaline phosphatase, $\beta$-galactosidase which represent the labelling enzymes most commonly used at present.

A standard reagent is constituted by the radioactive iodine. The molecules of the non-immune type are constituted, for example, by the labelled protein A. The radioactive labelling is most usually performed by means of iodine. It is obvious that other enzymes or radioactive reagents or even other forms of labelling can be used provided that they make it possible to reveal the antigen-antibody reaction under consideration.

The invention also relates to a diagnostic kit, characterized in that it contains:

at least one endogenous lectin or one of its subunits as defined above;
the solvents and agents necessary for the incubation and/or revelation steps.

Other characteristics and advantages of the invention are reported in the examples which follow relating to the isolation of partially purified CSL and to its use for the detection of the presence of anti-CSL antibodies in patients suffering from multiple sclerosis.

BRIEF DESCRIPTION OF THE FIGURES

In these examples, reference is made to the FIGS. 1 to 3 which represent respectively.

EXAMPLES

Figure 1:
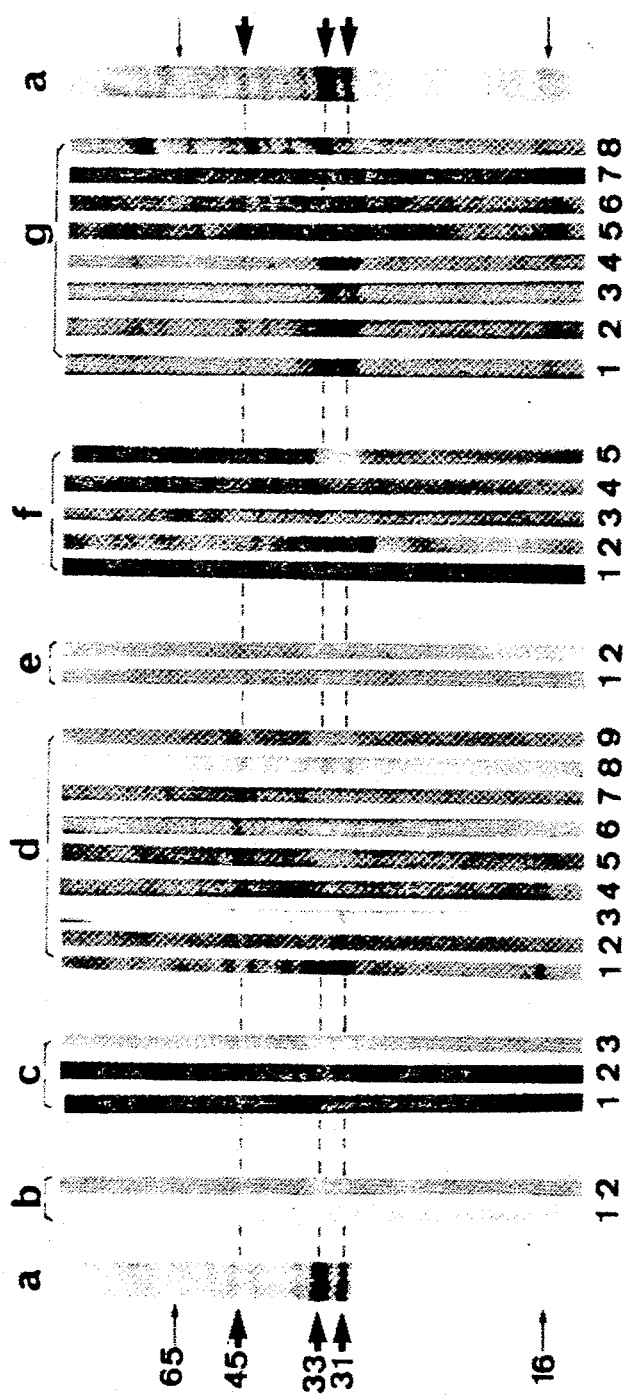
FIGS. 1 and 3 are photos of immunoblots obtained with samples of cerebrospinal fluid and plasma, respectively.

1. Preparation of a Partially Purified Antigenic Fraction of CSL

A specific solubilization of CSL is carried out using mannose as described in the article of ZANETTA et al previously mentioned, the CSL being derived from the cerebella of young rats. This and the subsequent operations are carried out at 4° C. using buffers to which are added protease inhibitors, namely phenylmethyl sulfonyl fluoride (PMSF) and p-tosyl-arginine methyl ester (0.1 and 0.3 mM, respectively), immediately prior to use.

The material solubilized in the presence of purified mannose (fraction TNM) is precipitated at 4° C. for 30 min. by the addition of 15% trichloroacetic acid, followed by centrifugation at 4° C.

The pellet is washed with pure methanol. It is dried under a gentle stream of air, then dissolved in the dissociating Laemmli buffer at a concentration of 1 mg/ml. It is then heated for 5 mn at 90° C. before electrophoresis is carried out.

The electrophoresis is carried out on a 13% polyacrylamide gel in the presence of SDS in the Laemmli buffer system on gel slabs 0.75 mm thick.

200 $\mu$l of a fraction enriched in CSL is loaded over a length of 130 mm and the migration is allowed to proceed for 6 hours under a constant current of 15 mA. The gel is transferred to nitrocellulose filters according to standard techniques.

After 4 h of transfer under constant voltage (36 V), at an intensity of 0.4 Amp., the edge of the blot is stained with Amido Black ®. The remainder of the nitrocellulose filter is saturated with a solution of bovine serum albumin or BSA (3%) in a Tris-HCl buffer (10 mM), pH 7.2 containing 150 mM of NaCl (TBS buffer) for 2 hours at room temperature.

The filter is washed with water and stored in water at 4° C. until it is used.

2. Incubation of the Antigenic Fraction with a Sample of Cerebrospinal Fluid from Patients Suffering from Various Neurological Diseases The nitrocellulose filter previously obtained is cut into strips 2 mm wide which are transferred to the lanes of an incubation vessel containing 0.75 ml of a 3% solution of BSA in the TBS buffer.

After incubation with gentle shaking for at least 1 hour at room temperature, 0.75 ml of cerebrospinal fluid is added.

The strips are subjected to shaking for 3 hours at room temperature, then are washed 15 times during a period of 2 hours, incubated for 10 min. in 3% BSA in the TBS buffer and rinsed with TBS for a further period of 2 hours.

3. Labelling and Revelation of the Antigen-Antibody Complex

BSA (1.5 ml of a 3% solution in TBS) is added to the strips obtained after rinsing and they are incubated for 30 min. at room temperature before the addition of goat anti-human IgG labelled with HRP or alkaline phosphatase (final dilution 1/500). The IgGs are obtained from the IMMUNOTECH Company or PELFREEZ BIOCHEMICALS.

The samples are shaken for about 14 hours at 4° C. and rinsed as described above.

The revelation of the samples is carried out according to the technique using chloronaphthol in the case of HRP and with a PROMEGA ® substrate in the case of alkaline phosphatase.

After reaction at room temperature, the strips are washed with water and dried between filter papers.

The positive samples correspond to those showing staining of the bands having MWs of 45, 33 or 31.5 kDa characteristic of CSL. This staining of the bands of CSL does not appear in the experiments performed in the absence of antibodies from the cerebrospinal fluid or if cerebrospinal fluid from patients suffering from neurological diseases other than multiple sclerosis is used.

4. Results

The photo shown in FIG. 1 shows a set of samples of immunoblots making it possible to detect the presence of anti-CSL antibodies in the cerebrospinal fluid of patients suffering from multiple sclerosis or other neurological diseases.

The results shown in FIGS. a) to g) correspond to the following situations:

a) staining with the aid of Amido Black ® of a preparation of protein used as antigen (fraction TNM of cerebella of young rats enriched in CSL). The presence of bands at 31.5, 33 and 45 kDa, characteristic of the subunits of the CSL, are observed in this partially purified preparation;

b) staining obtained in the absence of cerebrospinal fluid and by using goat anti-human antibodies labelled with HRP or AKP;

c) pattern obtained by using the cerebrospinal fluid of patients showing subarachnoid hemorrhages due to mechanical traumas. A background stain is observed in the absence of defined stained bands;

d) and g) correspond to the immunodetection of the CSL bands using the cerebrospinal fluid of patients with multiple sclerosis as sources of anti-CSL antibodies; the staining of the antigen-antibody complex is carried out using anti-human immunoglobulins labelled with HRP or AKP. It can be seen that the CSL subunits stained vary from patient to patient. The subunit of 31.5 kDa is stained in d) 1-3, the subunit of 45 kDa in d) 4-9. In a few cases, the CSL subunits of 31.5 and 33 kDa are intensely stained with a staining pattern different from that of the 45 kDa subunit;

e) and f) correspond to the same experiments but with the cerebrospinal fluid of patients suffering from other neurological diseases than multiple sclerosis. e) corresponds to non-infectious diseases not affecting the blood-brain barrier and f) to cases of viral meningitis. In 4 cases, a band at 67 kDa was stained subsequent to an immunological reaction. In one patient of the experimental series, this band is only observed during the acute phases of the disease. Bands of 40 kDa and 27 kDa are detected in a few cases.

These results show that the immunoblots of patients suffering from multiple sclerosis differ completely from those of patients suffering from other neurological diseases. The bands are not stained when cerebrospinal fluid is not added (see FIG. 1b)) or when the cerebrospinal fluid is obtained from patients having pathologies different from multiple sclerosis (FIG. 1c), 1e) and 1f)).

255 samples of cerebrospinal fluid were analysed during the course of these experiments, corresponding to more than 240 different patients. In the case of samples analysed twice or more, the results are always reproducible for the patients with diagnoses of multiple sclerosis.

Figure 2A:
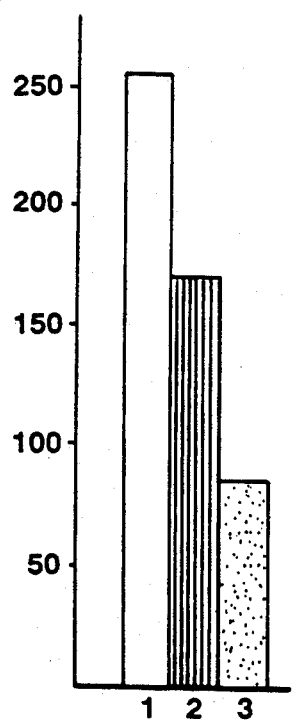
FIGS. 2a, 2b, 2c shows the distribution histograms of diagnoses.
Figure 2B:
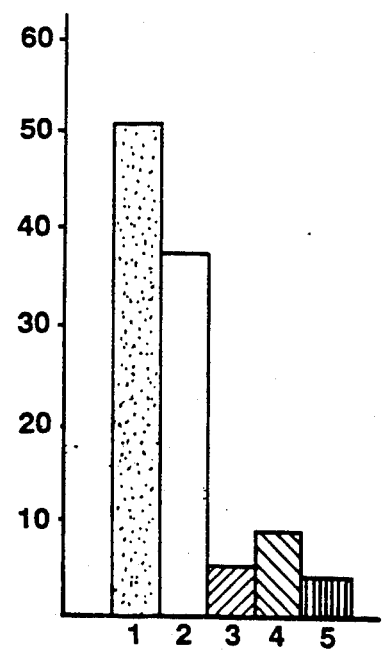
Figure 2C:
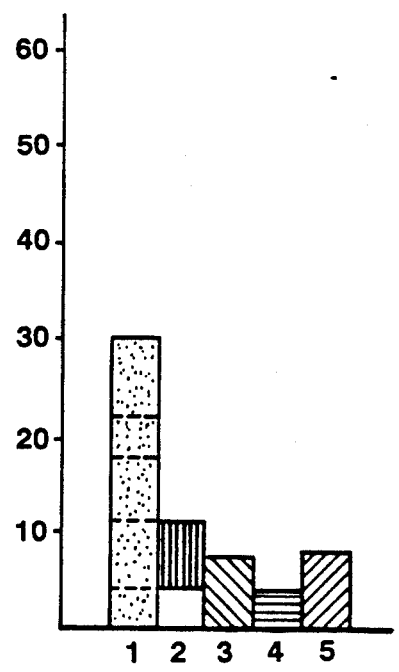

A summary of these results is presented in FIG. 2 which gives:

a—the sample distribution giving positive and negative results on analysis by means of an immunochemical test with CSL as antigen (1: total number of samples; 2: negative samples; 3: positive samples).

b—corresponds to the distribution of multiple sclerosis samples giving positive tests and classed as diagnosed, probable and possible, and tests giving negative results (1: total positive samples; 2-4: multiple sclerosis clinically diagnosed, probable and possible giving respectively positive tests; 5: multiple sclerosis, clinically diagnosed to give negative tests.

c—corresponds to the distribution of samples with a diagnosis different from multiple sclerosis giving positive reactions in the test (1: total samples; 2: polyneuropathies (white) and cerebal and pyramidal sydromes (dark); 3: meningitis; 4: hydrocephalus; 5: other diseases.

Negative results were obtained with 170 different cerebrospinal fluid samples derived from patients with various neurological diseases other than multiple sclerosis (dementia, Parkinson, vestibular syndromes, pseudobulbar syndromes, extrapyramidal syndromes, pains, lumbago, meningitis, hemorrhages, etc . . . ).

A set of samples corresponding to patients with hemorrhagic meningitis shows a background stain and a specific stain of a band at 67 kDa unrelated to CSL bands.

For 51 cases of multiple sclerosis (including clinically diagnosed multiple sclerosis, probable multiple sclerosis and possible multiple sclerosis), staining of the CSL bands is found in 47 cases. Negative results are obtained in only 4 cases. These 4 cases correspond to clinically diagnosed multiple sclerosis. In 30 cases, staining of the CSL bands is detected without diagnosis of multiple sclerosis. These cases correspond to a small number of diseases including the polyneuropathies (4 cases), cerebral and pyramidal syndromes (6 cases), olivo-ponto-cerebeller atrophies (1 case); meningitis (7 cases), hydrocephalus (4 cases) and other isolated diseases (septicemia, BROWNSEQUARD C8D1, tumor and epilepsy, dysesthesia, post-radiation leucoencephalitis, peripheral PF). These cases will be the object of a specific examination in NMRI.

By defining the specificity of the test as the ratio of the real true negative samples to the sum of the real negative samples and the false positive samples a minimum value of 85% is obtained which shows the high specificity of the test.

The values relating to the sensitivity are of the order of 93.5% (ratio of real positive samples to the sum of real samples and false negative samples).

These results show that the demonstration of the presence of anti-CSL antibody constitutes a good indicative criterium for a diagnosis of multiple sclerosis.

5. Utilization of Plasmas

The plasmas obtained after centrifugation of the blood collected on heparin are frozen and stored at −80° C. until used in the test.

Figure 3:
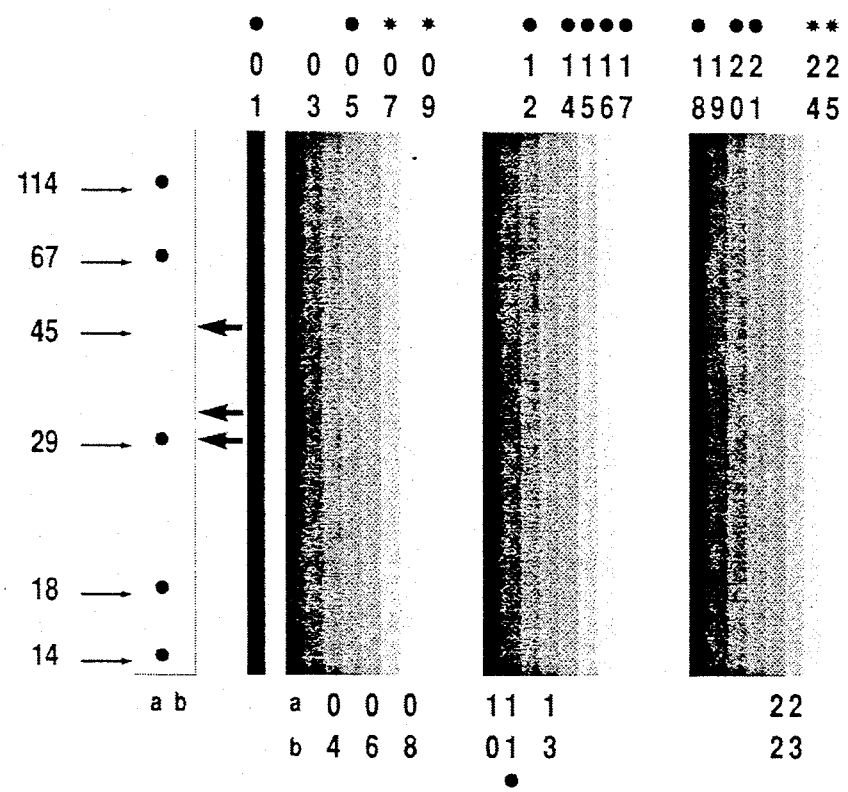

The results of the test using the immunoreplica technique for the presence of anti-CSL antibodies in a series of plasma samples from patients suffering from various neurological diseases are shown in FIG. 3.

a) and b) show the staining with Amido Black: a) markers of molecular mass (mass expressed in kDa) and b) proteins used for the test (the arrows indicate the position of the characteristic subunits of the CSL (31.5, 33 and 45 kDa).

The samples giving positive results are numbered at the top, the others along the bottom. The samples marked with an asterisk are those for which the diagnosis of multiple sclerosis was concluded.

A high intensity of staining of the bands at 31.5 and 33 kDa is noted in the case of most of the patients suffering from MS. A negative result (in the plasma as in the CSF) was obtained in the case of sample No. 11 which did not show images of patches by nuclear magnetic resonance imaging. The samples marked with an asterisk correspond to a patient suffering from polyneuritis, whose plasma was sampled before (07 and 24) and after (08 and 25) plasmapheresis. At low concentrations of plasma (1.5 μl for the test), a diminution of the anti-CSL antibodies is observed after plasmaphersis, but they remain detectable at higher concentrations (15 μl of plasma for the samples 24 and 25). The sample No. 21 corresponds to a MS with intrathecal synthesis of IgA since it gave an initial negative result with the CSF after revelation of the antibody bound by anti-IgGs. The utilization of anti-Ig instead of anti-IgG thus makes it possible to reveal this case as positive.

We claim:

1. A method for diagnosing multiple sclerosis comprising the steps of:
   (a) contacting a fluid sample taken from a patient, said fluid sample being selected from the group consisting of cerebrospinal fluid, blood, serum and plasma, with rat cerebellar soluble lectin, said lectin having an affinity for glycans rich in mannose or atleast one a subunit of said lectin, under conditions allowing an immunological reaction between said lectin or its subunits, and antibodies present in the fluid sample of the patient to form an immunological complex; and
   (b) detecting said immunological complex, if present, the presence of said immunological complex indicating multiple sclerosis.

2. The method according to claim 1, wherein one or more protein subunits of said lectin is used.

3. The method according to claim 2, wherein the contacting step is performed by incubation at room temperature in a buffer.

4. The method according to claim 3, wherein the detecting step of the immunoglobulins bound to said rat cerebellar soluble lectin, said lectin having an affinity for glycans rich in mannose, or a subunit of said lectin, is carried out by using labelled anti-Ig-human immunoglobulins, labelled anti-IgG immunoglobulins, labelled Protein A, or labelled Protein G.

5. The method according to claim 2, wherein the detecting step of the immunoglobulins bound to said rat cerebellar soluble lectin, said lectin having an affinity for glycans rich in mannose, or a subunit of said lectin, is carried out by using labelled anti-Ig-human immunoglobulins, labelled anti-IgG immunoglobulins, labelled Protein A, or labelled Protein G.

6. The method according to claim 1, wherein the cerebellar soluble lectin or one or more of the cerebellar soluble lectin subunits having a MW of 45 kDa, 33 kDa or 31.5 kDa, are used.

7. The method according to claim 1, wherein the contacting step is performed by incubation at room temperature in a buffer.

8. The method according to claim 1, wherein the detecting step of the immunoglobulins bound to the cerebellar soluble lectin or a subunit of said lectin, is carried out by using either labelled anti-Ig-human immunoglobulins or labelled anti-IgG immunoglobulins, or labelled Protein A or labelled Protein G.

9. The method according to claim 2, wherein the cerebellar soluble lectin or one or more of the cerebellar soluble lectin subunits, having a MW of 45 kDa, 33 kDa or 31.5 kDa, are used.

10. The method according to claim 9, wherein the contacting step is performed by incubation at room temperature in a buffer.

11. The method according to claim 9, wherein the detecting step of the immunoglobulins bound to said rat cerebellar soluble lectin, said lectin having an affinity for glycans rich in mannose, or a subunit of said lectin, is carried out by using labelled anti-Ig-human immunoglobulins, labelled anti-IgG immunoglobulins, labelled Protein A, or labelled Protein G.

12. A method for detecting the presence of antibodies which indicate a demyelinating neuropathy other than multiple sclerosis in a sample comprising the steps of:
   (a) contacting a fluid sample selected from the group consisting of human cerebrospinal fluid, human blood, human serum, and human plasma, with rat cerebellar soluble lectin, said lectin having an affinity for glycans rich in mannose, or a subunit of said lectin, under conditions allowing an immunological reaction between said lectin or its subunits and antibodies present in the fluid sample to form immunological complexes; and
   (b) detecting said immunological complexes, if present, wherein the presence of one of said complexes that comprises said lectin or lectin subunit having a molecular weight of 31.5 kilodaltons, 33 kilodaltons, or 45 kilodaltons, and the presence of at least one other of said complexes that comprises said lectin or lectin subunit having a molecular weight of other than 31.5 kilodaltons, 33 kilodaltons, or 45 kilodaltons, indicates a demyelinating neuropathy other than multiple sclerosis.

13. A diagnostic kit for detecting multiple sclerosis and other demyelinating neuropathies comprising:
   (a) at least one rat cerebellar soluble lectin, said lectin having an affinity for glycans rich in mannose, or a subunit of said lectin, and
   (b) the solvents and agents necessary for the incubation and detection of bound human antibodies to said cerebellar soluble lectin, wherein said agents for detecting bound human antibodies are labelled anti-Ig-human immunoglobulins.

* * * * *

UNITED STATES PATENT AND TRADEMARK OFFICE
CERTIFICATE OF CORRECTION

PATENT NO. : 5,225,352
DATED : July 6, 1993
INVENTOR(S) : Jean-Pierre Zanetta et al It is certified that error appears in the above-indentified patent and that said Letters Patent is hereby corrected as shown below:

Claim 1, column 7, line 37, delete "atleast" and insert therefor -- at least --;

Claim 3, column 7, line 47, delete "2" and insert therefor -- 1 --;

Claim 4, column 7, line 50, delete "3" and insert therefor -- 2 --;

Claim 5, column 7, line 58, delete "2" and insert therefor -- 7 --;

Claim 6, column 8, line 5, after "subunits" insert -- , --; and

Claim 7, column 8, line 7, delete "1" and insert therefor -- 2 --.

Signed and Sealed this

Tenth Day of May, 1994

Attest:

BRUCE LEHMAN

*Attesting Officer*  *Commissioner of Patents and Trademarks*